US00RE39664E

(19) United States
(12) Reissued Patent
Gordon et al.

(10) Patent Number: US RE39,664 E
(45) Date of Reissued Patent: May 29, 2007

(54) LATERAL FLOW CHROMATOGRAPHIC BINDING ASSAY DEVICE

(75) Inventors: Julian Gordon, Lake Bluff, IL (US); Charles Stuart Gredell Pugh, Middleton, WI (US)

(73) Assignee: Inverness Medical Switzerland GmbH, Zug (CH)

(21) Appl. No.: 08/561,215

(22) Filed: Nov. 21, 1995

Related U.S. Patent Documents

Reissue of:
(64) Patent No.: 4,956,302
Issued: Sep. 11, 1990
Appl. No.: 07/355,043
Filed: May 15, 1989

U.S. Applications:
(63) Continuation of application No. 08/322,027, filed on Oct. 12, 1994, now abandoned, which is a continuation of application No. 07/942,493, filed on Sep. 9, 1992, now abandoned, which is a continuation of application No. 07/095,801, filed on Sep. 11, 1987, now abandoned.

(51) Int. Cl.
*G01N 33/58* (2006.01)

(52) U.S. Cl. ..... 436/161; 422/56; 422/58; 422/70; 422/101; 435/7.9; 435/7.92; 435/7.95; 435/808; 435/810; 435/962; 435/969; 435/970; 436/162; 436/169; 436/170; 436/172; 436/178; 436/518; 436/530; 436/810; 436/825

(58) Field of Classification Search ..... 435/7.9, 435/7.92–7.95, 210, 803, 810, 962, 969, 435/970; 436/518, 530, 169, 170, 810, 825; 422/56, 58, 70, 101
See application file for complete search history.

(56) References Cited

U.S. PATENT DOCUMENTS

| | | | | | |
|---|---|---|---|---|---|
| 3,723,064 | A | | 3/1973 | Liotta | 435/810 X |
| 3,915,647 | A | | 10/1975 | Wright | 435/810 X |
| 4,094,647 | A | * | 6/1978 | Deutsch | |
| 4,168,146 | A | | 9/1979 | Grubb et al. | |
| 4,189,304 | A | | 2/1980 | Adams et al. | 422/56 X |
| 4,235,601 | A | * | 11/1980 | Deutsch | |
| 4,255,575 | A | | 3/1981 | Grisar et al. | 544/394 |
| 4,271,119 | A | | 6/1981 | Columbus | 422/50 |
| 4,323,536 | A | | 4/1982 | Columbus | 422/56 |
| 4,361,537 | A | * | 11/1982 | Deutsch et al. | 435/7.9 |
| 4,366,241 | A | * | 12/1982 | Tom et al. | 435/7.9 X |
| 4,391,904 | A | | 7/1983 | Litman et al. | 435/7.9 |
| 4,623,461 | A | | 11/1986 | Hossom et al. | 210/445 |
| 4,678,757 | A | | 7/1987 | Rapkin et al. | 436/169 |
| 4,693,834 | A | | 9/1987 | Hossom | 210/767 |
| 4,740,468 | A | * | 4/1988 | Weng et al. | 435/7.9 |
| 4,748,115 | A | * | 5/1988 | Steaffens | 435/21 |
| 4,761,381 | A | | 8/1988 | Blatt et al. | 436/165 |
| 4,861,711 | A | * | 8/1989 | Friesen et al. | 436/518 X |
| 4,943,522 | A | * | 7/1990 | Eisinger et al. | 435/7.1 |
| 4,956,275 | A | * | 9/1990 | Zuk et al. | 435/7.9 |
| 4,960,691 | A | * | 10/1990 | Gordon et al. | 435/6 |
| 4,981,786 | A | * | 1/1991 | Dafforn et al. | 435/7.9 |
| 5,030,558 | A | * | 7/1991 | Litman et al. | 435/7.91 |
| 5,079,142 | A | * | 1/1992 | Coleman et al. | 435/7.92 |
| 5,120,643 | A | * | 6/1992 | Ching et al. | 435/7.92 |

FOREIGN PATENT DOCUMENTS

| | | | | |
|---|---|---|---|---|
| EP | 0 088 636 | | 3/1983 | |
| EP | 0168689 | * | 1/1986 | 435/5 |
| EP | 0 183 442 | | 6/1986 | |
| EP | 0 262 328 | | 7/1987 | |
| EP | 0 267 006 | | 5/1988 | |
| EP | 0 296 724 | | 12/1988 | |
| EP | 0 322 340 | | 6/1989 | |
| WO | 88/08534 | | 11/1988 | |

* cited by examiner

*Primary Examiner*—Christopher L. Chin
(74) *Attorney, Agent, or Firm*—Jennifer A. Zarutskie; Foley Hoag LLP

(57) ABSTRACT

The present invention relates to improved specific binding assay devices comprising a chromatographic medium including a reaction site at which a specific binding reagent is immobilized, a sample application well located adjacent to the chromatographic medium and offset upstream from the reaction site, and liquid absorption blotter offset downstream from the reaction site.

14 Claims, 1 Drawing Sheet

LATERAL FLOW CHROMATOGRAPHIC BINDING ASSAY DEVICE

Matter enclosed in heavy brackets [ ] appears in the original patent but forms no part of this reissue specification; matter printed in italics indicates the additions made by reissue.

*This application is a continuation of application Ser. No. 08/322,027, filed Oct. 12, 1994 which is a continuation of application Ser. No. 07/942,493, filed Sep. 9, 1992.*

BACKGROUND OF THE INVENTION

The present invention relates generally to methods and devices for carrying out specific binding assays. More specifically, the invention relates to methods for the use of chromatographic transport for the movement of reagents and reactive sample components.

The use of specific binding assays has been found to be of great value in a variety of clinical and other applications. Such assays involve the detection and determination of an analyte substance which is a member of a specific binding pair consisting of a ligand and a receptor. The ligand and the receptor are related in that the receptor specifically binds to the ligands, being capable of distinguishing the ligand from other sample constituents having similar characteristics. Specific binding assays include immunological assays involving reactions between antibodies and antigens, DNA and RNA hybridization reactions and other specific binding reactions such as those involving hormone and other biological receptors. Specifically binding assays may be practiced according to a variety of formats well known in the art. Such assays include competitive binding assays, "direct" and "indirect" sandwich assays and agglutination assays.

Because the results of specific binding reactions are generally not directly observable, various techniques have been devised for labelling one member of the specific binding pair in order that the binding reaction may be indirectly observed. Useful labels include radiolabels, chromophores and fluorophores the presence of which may be detected by means of radiation detectors, spectrophotometers or the naked eye. Where members of a specific binding pair are tagged with an enzyme label, their presence may be detected by the enzymatic activation of a reaction system including a signal generating substrate/cofactor group wherein a compound such as a dyestuff, is activated to produce a detectable signal.

Specific binding assay devices are known in the art comprising vertically arranged elements including (a) a porous capture material which is impregnated at a reaction site with member of a specific binding pair such as an antibody or an antigen; (b) a removable prefilter disposed above the capture material and (c) a blotter disposed below the capture material. A sample liquid such as blood, serum or other biological fluid is added to the device wherein the prefilter removes particulates and other impurities from the sample which would otherwise be trapped on top of the specific binding capture material. Analyte substances within the sample are trapped by means of specific binding reactions with their specific binding partners on the capture material. Non-analyte components of the sample solution pass through the capture material and are absorbed by the blotter. Wash steps may be carried out to remove non-analyte components from the capture material and additional reagents such as enzyme substrates, cofactors and dye precursors, may be added to the capture material in order to indicate the presence or absence of analyte at the reaction site. The prefilter must then be removed in order that the presence or absence of analyte at the reaction site may be virtually determined. Such assay devices are rapid and generally reliable but suffer from limitations in capture efficiency and sensitivity because most of the analyte in the sampling material flows around rather than through the reaction site on the capture material.

Various disclosures are of interest to the present application. Tom, et al., U.S. Pat. No. 4,366,241 discloses an immunoassay device comprising a relatively small test zone including a specific binding reagent, and a relatively large absorbing zone in liquid receiving relationship with said immunosorbing zone. Immunoassays for determining the presence of an analyte material are carried out by contacting the assay device with a sample solution, a solution containing enzyme labelled specific binding material and a solution containing an enzyme catalyzed signal system. The solutions migrate through the immunosorbing zone into the liquid absorbing zone and the presence of analyte in the sample material is indicated by enzyme activation of the signal system.

Deutsch, et al., U.S. Pat. Nos. 4,094,647, 4,235,601 and 4,361,537 relate to immunological and other types of specific binding assays wherein reagents are transported by chromatographic solvent transport. According to one embodiment, a radiolabeled competitive binding assay kit comprises a strip capable of transporting a developing liquid by capillarity having a first zone for receiving a sample, a second zone impregnated with a first reagent capable of being transported by the developing liquid and a third zone impregnated with a second reagent. In addition, the devices comprise a measuring zone and a retarding element which may be either the second reagent or the material of the strip. The first reagent is capable of reacting with one of the group consisting of (1) the sample, (2) the sample and the second reagent, and (3) the second reagent in competition with the sample, to form a product in an amount dependent on the characteristic being determined. A sample is contacted with the first zone and the strip is then dipped into the developing liquid to bring about transport of the sample and the first reagent to form the reaction product. The retarding element shows transport of either the product or the first reagent (the moving reagent) to spacially separate the two and the amount of the moving element is then measured at the measurement location.

Also of interest to the present invention is the disclosure of co-owned [and copending U.S. patent application Ser. No. 912,878 filed Sept. 29, 1986 by Gordon, et al.] *U.S. Pat. No. 4,960,691*, which is hereby incorporated by reference and which relates to devices for conducting specific binding assays utilizing the sequential chromatographic transport of analyte and reagent materials. Wash and addition steps are inherently carried out and liquid "microcircuitry" can be programmed to carry out a variety of multistep procedures and to avoid the premature mixing of sample materials and reagents. Specifically, the Gordon[.] et al., sequential transport application relates to devices which comprise a test strip for the detection of an analyte in a sample comprising a length of chromatographic material having the capacity for rapid chromatographic solvent transport of non-immobilized reagents and reactive sample components by means of a selected chromatographic solvent.

Of further interest to the present invention are the disclosures of Piasio, et al., U.S. Pat. No. 4,255,575 and Litman, et al., U.S. Pat. No. 4,391,904. These references relate to specific binding assay methods generally and disclose immobilization of enzyme substrates buffers and cofactors on solid phase matrices.

SUMMARY OF THE INVENTION

The present invention relates to devices and methods for determining the presence or amount of an analyte substance in a sample by means or one or more specific binding reactions. The devices include, a chromatographic medium having capillarity and the capacity for chromatographic solvent transport of one or more reactive sample components and non-immobilized reagents including a reaction site at which is present an immobilized reagent capable of binding a member from the group consisting of the analyte substance and a labelled specific binding material. The devices also include a sample application means located adjacent to the chromatographic medium and offset upstream from the reaction site, and a liquid absorption means offset downstream from the reaction site. A method for use of the device to determine the presence or amount of an analyte substance in sample includes the steps (a) applying a volume of a sample to be analyzed to the sample application means whereby the sample is transported along the chromatographic medium through the reaction site to the liquid absorption means, (b) contacting the labelled specific binding material to the reaction site, (c) removing unbound sample materials and unbound labelled specific binding materials from the reaction site and (d) determining the presence or amount of labelled specific binding material immobilized at the reaction site as an indication of the presence or amount of the analyte substance in the sample.

The unbound sample materials and unbound labelled specific binding materials may be removed from the reaction site by means of a wash step wherein a wash solution is applied to the reaction site, preferably by application through the sample application means. Alternatively, if the labelled binding material is sufficiently dilute, a wash step is not always necessary.

DETAILED DESCRIPTION

The present invention provides improved methods and devices for the practice of chromatographic specific binding assay techniques. Devices according to the invention are characterized by a high capture efficiency which is particularly advantageous in the use of the invention for diagnosis of pediatric and geriatric patients where the volume is of sample fluids obtainable from such patients may be limited. This high capture efficiency results from the chromatographic transport of sample and other reactive materials laterally through the reaction site which forces the materials to flow through a length of chromatographic media containing specific binding agents rather than through or around a narrow thickness of impregnated medium.

The devices are suitable for analysis of samples with heavy loads of particulate matter without the necessity of a prefilter. Particulate matter does not interfere with analyte determination at the location of the reaction site, but instead accumulates at the interface of the sample application means and the chromatographic material. Nevertheless, prefilters, and particularly non-removable ones, may be used and fitted into sample application means where samples comprise especially heavy loads of particulate matter, for example, whole blood.

The devices of the present invention comprise a chromatographic medium with a reaction site, a sample application means located adjacent to the medium and offset upstream from the reaction site and a liquid absorption means located downstream from the reaction site. Present at the reaction site is an immobilized reagent capable of binding a member from the group consisting of said substances and a labelled specific binding material. The chromatographic medium and sample application and liquid absorption means are preferably disposed in a holder. Sample materials and reagents are added together or sequentially to the sample application means, which may comprise an area offset from the reaction site, a well, an absorbent pad, or volumetric delivery device in contact with the chromatographic medium. Preferably, the sample application means is a well or absorbent pad, such as may be fashioned from blotter material. The sample materials and reagents are absorbed into the chromatographic medium and are chromatographically transported along the medium and laterally through the reaction site. Analyte substance and reagent materials may be immobilized by a specific binding reaction at the reaction site while non-analyte sample components and non-immobilized reagents are transported through the chromatographic medium to the liquid absorption means located downstream from the reaction site.

Figure 1:
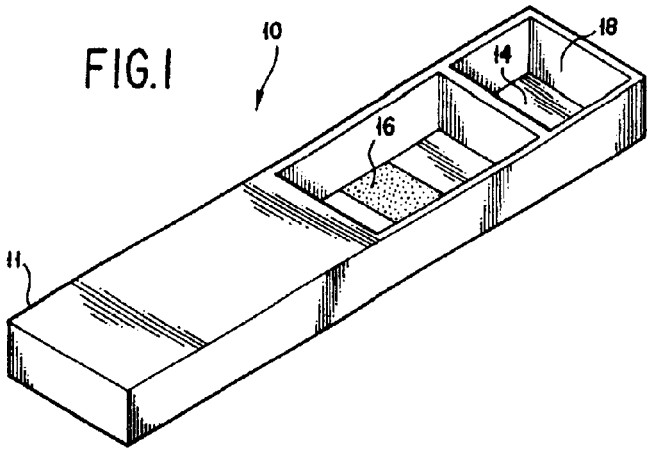
FIG. 1 depicts a perspective view of a device according to the present invention.
Figure 2:
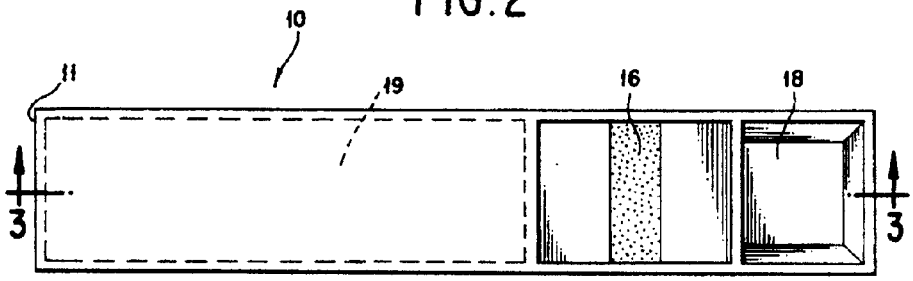
FIG. 2 depicts a top view of the device depicted in FIG. 1.
Figure 3:
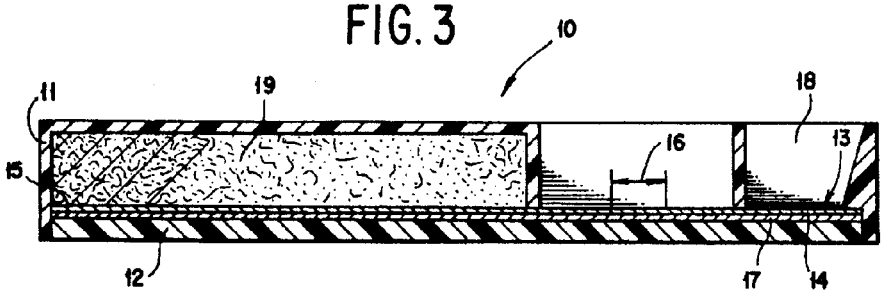
FIG. 3 depicts a view along line 3—3 of the device depicted in FIG. 2.

Referring to the drawings, FIGS. 1 through 3, depict a device (10) for the detection of an analyte in a sample liquid comprising an upper housing portion (11), a lower housing portion (12), a length of chromatographic medium (13) with a first end (14) at which chromatographic solvent transport begins, a second end (15) at which chromatographic solvent transport ends and a reaction site (16) at which is immobilized a reagent capable of binding a member from the group consisting of the analyte substance and a labelled specific binding material. The device (10) further comprises a backing strip (17) adjacent to the chromatographic medium (13), a sample well (18) defined by the upper housing portion (11) adjacent to the first end (14) of the chromatographic medium (13) and a blotter material (19) downstream from the reaction site (16) and adjacent to the second end (15) the chromatographic medium (13).

According to one procedure for use of the device (10) to perform sandwich-type assays, a volume of a sample to be tested for the presence of an analyte substance is added to the sample well. The sample material is absorbed into the chromatographic medium (13) where it begins to flow toward the second end (15). The sample material containing the analyte substance, if any, flows through the reaction site (16) at which a reagent is immobilized which is capable of specifically binding with any analyte substance so as to immobilize it at the reaction site (16). Non-analyte sample materials continue to flow through the chromatographic medium (13) toward the second end (15) where they are absorbed by the blotter material (19).

When transport of the sample material from the sample well (18) to the blotter material (19) is complete a labelled reagent material capable of specifically binding with the analyte substance is added to the sample well (18) such that it is absorbed by the chromatographic medium (13) and transported through the reaction site (16) to the second end (15) of the medium where it is absorbed by the blotter material (19). When any of the analyte substance is immobilized at the reaction site (16) the labelled reagent material reacts with the analyte substance and is also immobilized. Where the reagent material is labelled with a radiolabel, a chromophore or a fluorophore the presence of the labelled material and hence the analyte substance may be detected at the reaction site. Where the reagent material is enzyme-labelled, additional reagents such as enzyme substrates, cofactors and dye precursors may be added to the sample well (18) or directly to the reaction site (16) in order to indicate the presence of the analyte substance.

According to two alternative embodiments, the labelled specific binding material may be included or dried in the chromatographic medium, upstream of reaction site or in the absorbent material of the sample application means such that it is reconstituted by addition of the sample.

The device (10) according to FIGS. 1 through 3 may also be modified to perform competition-type specific binding assays. According to one such method, the labelled specific binding reagent may be selected to compete with the analyte substance for binding with the reagent immobilized at the reaction zone (16) which is capable of binding with both. The quantity of the analyte substance present in the sample will determine the preportion of a predetermined amount of labelled specific binding material that binds at the reaction site (16). Adjustments [Of] *of* the quantity and/or binding affinity of the labelled specific binding material can be made in order to determine the quantity of analyte present in the sample.

Various other specific binding assays may be carried out on the devices of the present invention. As an example, the chromatographic medium may be impregnated at additional reaction sites with various immobilized specific binding agents. Such additional reaction sites may be used for the detection of additional analyte substances or may be used, as in a comparison-type assay to quantify the amount of analyte substance present in a sample. Additional reaction zones may be used to capture substances that interfere with accurate determination of the analyte.

The chromatographic medium may be impregnated with other reagents and materials including dye compounds, enzyme substrates, coenzymes and cofactors which react with enzyme labels to produce color signals as is well known in the art. According to one aspect of the present invention, where the labelled specific binding agents are enzyme-labelled the enzyme label being characterized in that its presence may be determined by reaction with members of a signal generating substrate/cofactor group, a first member of the signal generating substrate/cofactor group may be immobilized at a reaction site on the chromatographic medium. A second member of the substrate/cofactor group may be added at an appropriate time to activate the signal generating system if an enzyme label is present. By preimpregnating the reaction site with a member of the signal generating substrate/cofactor group, an additional step is avoided and problems relating to the instability or insolubility of substrates, cofactors and dye precursors when stored together are avoided. Moreover, certain members of the signal generating group of compounds may have low chromatographic mobility with the result that pre-impregnation at the reaction site is particularly preferred.

The devices may be housed singly, in pairs, or in multiple configurations. The housing should preferably be watertight to prevent leakage and may be manufactured from a variety of inert materials, with polymer materials being preferred for their ease of fabrication. The sample well should be of sufficient volume to contain any required amount of sample or reagents to be used with the invention. Where the liquid absorption means is enclosed within the housing of the device, it should be provided with sufficient volume that sample, wash, and reagent materials applied to the device during assay procedures may all be absorbed. According to a preferred embodiment of the present invention wherein the chromatographic media is a strip of nitrocellulose material 0.4 cm wide, sample and reagent volumes ranging from 10 μl to 150 μl are suitably accommodated.

The reaction site is located downstream from the sample application means and is visible to view from either side, either being unenclosed or covered with a transparent material. The reaction site is preferably unenclosed, thus facilitating observation of the presence or absence of signals from the site and also allowing the addition of reagents and/or wash solutions to the reaction site.

The liquid absorption means located downstream from the reaction site absorbs sample materials, reagents and wash solutions and thus allows chromatographic transport of sample and other materials from the first end of the chromatographic medium through the reaction site to the second end of the medium. Without such absorption chromatographic transport would cease and the efficiency advantage resulting from the lateral flow of sample through the reaction site would be lost.

The liquid absorption means can include the chromatographic medium itself wherein sample and reagent materials are transported and absorbed by an extended length of the medium. A particularly preferred aspect of the invention is that wherein the liquid absorption means is located adjacent to the chromatographic medium and is offset downstream from the reaction site. Locating the absorption means adjacent to the chromatographic medium provides additional absorption capacity. Offsetting the absorption means downstream from the reaction site ensures that sample materials, and all other materials introduced upstream of the reaction site flow primarily laterally and not vertically through the reaction site.

The absorption means may consist of an extended length of chromatographic medium but preferably consists of a quantity of blotter material. Cellulosic blotter materials derived from wood pulp or cotton are suitable. The blotter material need not have dimensions similar to those of the chromatographic medium and is generally wider and thicker than the chromatographic medium. The blotter need only be adjacent to the chromatographic medium such that fluid from the chromatographic medium can flow into the blotter. A particularly preferred material is James River Type 52 point blotter material (James River Paper Co., Inc., Richmond, Va.). The absorption means preferably must be capable of absorbing the entire volume of sample material and is preferably capable of absorbing the additional reagents and doing so rather rapidly.

Chromatographic media useful with the present invention include those chromatographic substrate materials having capillarity and the capacity for chromatographic solvent transport of non-immobilized reagents and sample components. The chromatographic media used with the invention are preferably in the form of strips. While a wide variety of chromatographic materials such as woven and non-woven fibrous materials used for paper chromatography are suitable for use with the invention, the use of microporous or microgranular thin layer chromatography substrates is particularly preferred as the use of such materials improves the speed and resolution of the assays according to the invention. The materials should preferably be inert and generally not react physically or chemically with any of the sample components, reagents buffers or reaction products. Co-owned [and copending U.S. patent application Ser. No. 912,878 filed Sept. 29, 1986] *U.S. Pat. No.* 4,960,691 and U.S. [patent application Ser. No. 072,459 filed July 13, 1987]*Pat. No. 5,120,643*, the disclosure of which are hereby incorporated by reference, disclose a wide variety of suitable chromatographic substrate materials. Particularly preferred, however, is the use of a microporous nitrocellulose material with a pore size of 5 μm designated Type SMWP (Millipore Corp., Bedford, Massachusetts).

Because the chromatographic media of the device is preferably chemically inert, it may have to be activated at any reaction site where it is desired to immobilize a specific binding reagent against solvent transport. Various methods will be required to render the reagent immobilized according to the particular chemical nature of the reagent. Generally, when the media is nitrocellulose or a mixed nitrocellulose ester, no special chemical linkage is required for the immobilization of reagents. Various techniques may be used for other materials and reagents which include functionalization with materials such as carbonyldiimidazole, glutaraldehyde or succinic acid, or treatment with materials such as cyanogen bromide. Other suitable reactions include treatment with Schiff bases and borohydride for reduction of aldehyde, carbonyl and amino groups. DNA, RNA and certain antigens may be immobilized against solvent transport by baking onto the chromatographic material. Baking may be carried out at temperatures ranging from about 60° C. to about 120° C. for times varying from about five minutes to about 12 hours, but preferably at about 80° C. for about two hours.

Specific binding reagents useful with the present invention would be readily identifiable to one of skill in the art and include those materials which are members of a specific binding pair consisting of a ligand and a receptor. The ligand and receptor are related in that the receptor specifically binds to the ligands, being capable of distinguishing the ligand from other materials having similar characteristics. The methods and devices according to the present invention are particularly useful in the practice of immunological assay techniques where the specific binding reagents are antigens and antibodies including antibody fragments and synthetic antibodies. Specific binding materials such as avidin, biotin, strepatavidin and antibiotin may also be labelled and utilized in specific binding chromatographic assays according to the invention. The methods, kits and devices may also prove useful in the practice of DNA and RNA hybridization assays and other specific binding assays such as those involving receptors for hormones or other biologically active agents.

Blocking agents useful in preparation of devices for the specific binding of the present invention are those agents capable of blocking excess binding sites on the chromatographic media which might hinder chromatographic solvent transport of sample materials or reagents of the invention. In the construction of devices of the present invention, the chromatographic medium is impregnated with the reagent to be immobilized at the location desired. Once the reagent has been immobilized at the desired site, the strip is then preferably processed so as to block excess binding sites for other reagents or sample materials. Particularly suitable is the use of blocking solutions comprising proteins such as casein, gelatin, albumin or total serum. Such proteins are selected to not interfere with or cross-react with reagent materials of the assays. Blocking of the sites may preferably be conducted by dipping the chromatographic substrate materials in a solution of 0.2% casein in physiological saline and air drying the strip materials. Other methods include dipping in solutions of 0.1% gelatin or 0.1% bovine serum albumin followed by air drying of the substrate materials.

EXAMPLE 1

According to this example, sandwich-type immunoassay devices for the detection of Hepatitis B surface antigen (HBsAg) were constructed and used. Microporous nitrocellulose material with a thickness of approximately 0.15 mm and a pore size of 5μm (Millipore SMWP) was laminated to Mylar and adhesive (Monokote, Top Flite Models, Inc., Chicago, Ill.) at 60° to 65° C. in a film dryer apparatus. The membrane and backing was cut to strips 0.4 cm wide and 2.5 cm long. Anti-HBsAg antibodies (Abbott Laboratories, North Chicago, Ill.) (0.1–0.2 μl, 1.5 mg/ml) were applied to the reaction sites and incubated under ambient conditions for 15 minutes. Non-specific binding sites on the chromatographic medium were then blocked and cosubstrate bound by incubation for ten minutes at ambient temperature with a solution comprising 0.1% fish gelatin, 1% sucrose and 0.14 mg/ml nitro blue tetrazolium in 10 mM Tris and 150 mM NaCl (pH 7.6). The strips were then dried at 40° C. for about one hour and stored at ambient in the presence of a desiccant. Devices generally similar to the device of FIG. 1 through 3 were fashioned utilizing the impregnated strips and James River 52 point blotter material (1.0 cm by 2.4 cm) which was placed above the second end of the strips to function as a liquid absorption means.

To the sample application well of each test device was added a 30 μl sample of decalcified plasma which had been spiked with varying concentrations of HBsAg. After the sample had soaked into the first end of the nitrocellulose material, and had been transported through the reaction site to the second end of the nitrocellulose material, been absorbed by the blotter material a 15 μl aliquot of biotin labelled Anti-HBsAg antibodies (1 μg/ml) was added to each sample well. After this solution was transported through the device, a 15 μl aliquot of alkaline phosphatase labelled antibiotin (2 μg/ml) (Abbott Laboratories, North Chicago, Ill.) was added to each sample well and reaction sites were twice washed by addition to each sample well of 15 μl of wash solution comprising 1% [Triton X 100] *Triton X 100® brand of octylphenoxypolyethoxy ethanol nonionic detergent* Tris buffered saline solution. A 15 μl aliquot of developing solution comprising 0.5 mg/ml bromochloroindolylphosphate, 0.1 mg/ml $MgCl_2$ and 1% 2-amino-2-methyl propanol (pH 9.8) was then added to each sample well and a color reaction was allowed to develop for five minutes before the reaction was inhibited by addition of 15 μl of a 10 mM ethylene diamine tetraacetic acid (EDTA) solution. Sample solutions containing no HbsAg produced no signal, the reaction site was white. Sample solutions containing as little as 0.1 ng/ml HbsAg produced readily visible blue-gray spots at the reaction site. The total assay time was 25 minutes.

EXAMPLE 2

According to this example, sandwich-type immunoassay devices for the detection of HbsAg were constructed and used wherein the labelled specific binding material is labelled with colloidal gold particles according to the method of co-owned [and copending U.S. Ser. No. 072,459] *U.S. Pat. No. 5,120,643*. The device and materials used were identical to that described according to Example 1, with the exception that nitro blue tetrazolium was omitted from the blocking solution.

To the sample well of each device was added a 50 μl sample of recalcified plasma which had been spiked with varying amounts of HBsAg. After the sample had soaked into the first end of the nitrocellulose material, a 50 μl aliquot of anti-HBsAg antibodies labelled with 40 nm colloidal gold particles adsorbed at 5 μg/ml (Abbott Laboratories) was added to each sample well. The total time for the assay was 15 minutes. Sample solutions containing no HBsAg produced no signal over background. Sample solutions as little as 1.0 ng/ml of HBsAg produced visible purple spots at the reaction site. No wash step was required since the antibody gold particles were sufficiently dilute.

Numerous modifications and variations in practice of the invention are expected to occur to those skilled in the art upon consideration of the foregoing descriptions of preferred embodiments thereof. It is well within the skill in the art to practice the present invention according to a wide variety of methods and formats. Consequently, only such limitations should be placed on the invention as appear in the following claims.

What is claimed is:

1. A test device for determining the presence or amount of an analyte substance in a sample by means of one or more specific binding reactions comprising:

a *bibulous* chromatographic medium which extends throughout said device *and is free of chromatographic transport-facilitating agent*, defining a flowpath having capillarity and [the] capacity for chromatographic solvent transport of one or more reactive sample components and non-immobilized reagents; said chromatographic medium comprising (1) a prefiltering zone; (2) a reaction [site] *zone* disposed downstream from said prefiltering zone [at which is present] *containing* an immobilized reagent [capable of binding] *which specifically binds* a member *selected* from the group consisting of said analyte substance and a labeled specific binding material, and at which the presence or amount of immobilized specific binding material, [may be] *is capable of being* detected; and (3) a downstream zone free of said immobilized reagent disposed downstream from said reaction [site] *zone*,

[a sample application means selected from the group consisting of] *a single undivided* well [and an absorbent pad] *defined by a housing element comprising an upper and lower portion; wherein said upper portion defines the spatial boundaries of said well and said lower portion comprises a portion of said chromatographic medium which is upstream of said prefiltering zone, said well having sufficient capacity to hold a volume of sample for chromatographic movement of said volume of sample from said well to a liquid absorption means, said well being* located adjacent to and disposed in fluid contact with said prefiltering zone of said chromatographic medium and offset upstream from said reaction [site] *zone*, and

*said* liquid absorption means consisting of a quantity of blotter material disposed in fluid contact with said downstream zone of said chromatographic medium and offset downstream from said reaction [site] *zone*.

[2. The test device according to claim 1 wherein said sample application means consists of a well.]

[3. The test device according to claim 1 wherein said sample application means consists of an absorbent pad.]

4. The test device according to claim 1 wherein said well comprises a non-removable filter.

5. The test device according to claim 1 wherein a member of a signal generating substrate/cofactor group is immobilized at said reaction zone.

6. The test device according to claim 5 wherein nitroblue tetrazolium is immobilized at said reaction zone.

7. A method for determining the presence or amount of an analyte substance in a sample which method utilizes a device comprising:

a *bibulous* chromatographic medium which extends throughout said device and *is free of chromatographic transport-facilitating agent*, defining a flowpath having capillarity and [the] capacity for chromatographic solvent transport of one or more non-immobilized reagents and reactive sample components; said chromatographic medium comprising (1) a prefiltering zone; (2) a reaction [site] *zone* disposed downward from said prefiltering zone [at which is present] *containing* an immobilized reagent [capable of binding] *which specifically binds* a member *selected* form the group consisting of said anlayte substance and labeled specific binding material, and at which the presence or amount of immobilized labeled specific binding material [may be] *is capable of being* detected and (3) a downstream zone free of said immobilized reagent disposed downstream from said reaction [site] *zone*,

[a sample application means selected from the group consisting of] *a single, undivided* well [and an absorbent pad] *defined by a housing element having an upper and lower portion; wherein said upper portion defines the spatial boundaries of said well and said lower portion comprises a portion of said chromatographic medium which is upstream of said prefiltering zone, said well being of sufficient capacity to hold a volume of sample for chromatographic movement from said well to a liquid absorption means, said well being* located adjacent to and disposed in fluid contact with said prefiltering zone of said chromatographic [material] *medium* and offset upstream from said reaction [site] *zone*, and

[a] *said* liquid absorption means consisting of a quantity of blotter material disposed in fluid contact with said downstream zone of said [chromatographic] *chromatographic* medium and offset downstream from said reaction [site] *zone*, said method comprising:

(a) applying [a] *said* volume of said sample [sample application means] *to said well* whereby said sample *is free of chromatographic transport-facilitating agent and* is [transported] *absorbed* onto said chromatographic medium [at] *and is chromatographically transported through* said prefiltering zone and along said chromatographic medium through said reaction [site] *zone*, and said downstream zone to said [sample] *liquid* absorption means, (b) contacting said labeled specific binding material to said reaction [site] *zone*, and (c) determining the presence or amount of *said* labeled specific binding material immobilized at said reaction [sites] *zones* as an indication of the presence or amount of the analyte substance in the sample.

8. The method according to claim 7 wherein unbound sample materials and unbound specific binding materials are removed from the reaction zone by means of a wash step.

9. The method according to claim 7 wherein said unlabeled specific binding material participates in a specific binding reaction with said analyte substance.

10. The method according to claim 7 wherein said reaction [site] *zone* includes an immobilized member of a signal generating substrate/cofactor group, said method further comprising the step (c') of contacting one or more additional members of said signal generating substrate/cofactor group to said reaction site to initiate a signal generating reaction.

11. The method according to claim 10 wherein nitroblue tetrazolium is immobilized at said reaction [site] *zone* and bromochlorindolylphosphate is added to initiate a signal generating reaction.

*12. A test device for determining the presence or amount of an analyte substance in a sample by means of one or more specific binding reactions comprising:*

*a bibulous chromatographic medium-free of chromatographic transport-facilitating agent having capillarity and the capacity for lateral chromatographic transport of one or more reactive sample components and non-immobilized reagents, said medium including a reaction zone comprising an immobilized reagent which binds a member selected from the group consisting of said analyte substance and a labeled specific binding material, said reaction zone occupying less than the entire area of the medium such that there remains an upstream portion and a downstream portion;*

*a single undivided well defined by a housing element comprising an upper and lower portion; wherein said upper portion defines the spatial boundaries of said well and said lower portion comprises a part of said upstream portions, said well being in fluid contact with the upstream portion of said chromatographic medium and being of sufficient capacity to retain a volume of fluid sample for chromatographic movement of said volume of sample along said chromatographic medium from said well through said reaction zone and into a liquid absorption means;*

*said liquid absorption means consisting of a quantity of blotter material disposed in-fluid contact with said downstream zone of said chromatographic medium.*

*13. The test device according to claim 1 wherein said chromatographic medium is selected from the group consisting of nitrocellulose or mixed nitrocellulose ester.*

*14. The method according to claim 7 wherein said chromatographic medium is selected from the group consisting of nitrocellulose or mixed nitrocellular ester.*

*15. The test device according to claim 14 wherein said chromatographic medium is selected from the group consisting of nitrocellulose or mixed nitrocellulose ester.*

*16. The test device according to claim 12 wherein said well includes a non-removable filter.*

* * * * *